US008119037B2

(12) United States Patent
Zeika et al.

(10) Patent No.: US 8,119,037 B2
(45) Date of Patent: Feb. 21, 2012

(54) SQUARE PLANAR TRANSITION METAL COMPLEXES AND ORGANIC SEMICONDUCTIVE MATERIALS USING THEM AS WELL AS ELECTRONIC OR OPTOELECTRIC COMPONENTS

(75) Inventors: Olaf Zeika, Dresden (DE); Ansgar Werner, Dresden (DE); Steffen Willmann, Dresden (DE)

(73) Assignee: Novaled AG, Dresden (DE)

( * ) Notice: Subject to any disclaimer, the term of this patent is extended or adjusted under 35 U.S.C. 154(b) by 365 days.

(21) Appl. No.: 12/429,034

(22) Filed: Apr. 23, 2009

(65) Prior Publication Data

US 2010/0096600 A1    Apr. 22, 2010

Related U.S. Application Data

(60) Provisional application No. 61/105,842, filed on Oct. 16, 2008.

(51) Int. Cl.
*H01L 51/54* (2006.01)
(52) U.S. Cl. ............. 252/519.21; 252/500; 257/40
(58) Field of Classification Search ............ 252/500
See application file for complete search history.

(56) References Cited

U.S. PATENT DOCUMENTS

| | | | |
|---|---|---|---|
| 5,792,568 | A | 8/1998 | Emoto et al. |
| 6,908,783 | B1 | 6/2005 | Kuehl et al. |
| 6,984,591 | B1 | 1/2006 | Buchanan et al. |
| 2002/0042174 | A1 | 4/2002 | Kunugi et al. |
| 2002/0179885 | A1 | 12/2002 | Che et al. |
| 2003/0186080 | A1 | 10/2003 | Kamatani et al. |
| 2003/0205707 | A1 | 11/2003 | Chi-Ming |
| 2004/0065544 | A1 | 4/2004 | Igarashi et al. |
| 2004/0121184 | A1 | 6/2004 | Thompson et al. |
| 2004/0241492 | A1 | 12/2004 | Tokuda et al. |
| 2004/0262576 | A1 | 12/2004 | Thompson et al. |
| 2005/0221115 | A1 | 10/2005 | Tsuboyama et al. |
| 2005/0260449 | A1 | 11/2005 | Walters et al. |
| 2006/0071206 | A1 | 4/2006 | Spreitzer et al. |
| 2006/0208252 | A1 | 9/2006 | Wessels et al. |
| 2006/0258043 | A1 | 11/2006 | Bold et al. |
| 2007/0111025 | A1 | 5/2007 | Lennartz et al. |
| 2007/0135635 | A1 | 6/2007 | Stoessel et al. |
| 2007/0264524 | A1 | 11/2007 | Gessner et al. |
| 2008/0121870 | A1 | 5/2008 | Seth et al. |
| 2009/0318698 | A1 | 12/2009 | Hartmann et al. |
| 2010/0044683 | A1 | 2/2010 | Zeika et al. |

FOREIGN PATENT DOCUMENTS

| | | |
|---|---|---|
| DE | 4112793 | 10/1992 |
| GB | 1436230 | 5/1976 |
| JP | 63-126889 | 5/1988 |
| JP | 03-093593 | 4/1991 |
| JP | 03208689 | 9/1991 |
| WO | WO 2004/017043 | 2/2004 |
| WO | WO 2005/086251 | 9/2005 |
| WO | 2007/018065 | 2/2007 |
| WO | WO 2007134873 A1 * | 11/2007 |
| WO | 2008/061517 | 5/2008 |
| WO | 2008/061518 | 5/2008 |

OTHER PUBLICATIONS

Adachi, C. et al. "High-efficiency red electrophosphorescence devices," Appl. Phys. Lett. 2001, 78, 1622.
Beckert, R. et al., "Syntheses and properties of cycloamidines based on 4H-imidazoles," Z. Naturforschung B, vol. 61, No. 4 (2006).
Blochwitz, J., et al., "Low voltage organic light emitting diodes featuring doped phthalocyanine as hole transport material," Applied Physics Letters, vol. 73, No. 6, Aug. 10, 1998, pp. 729-731.
Chassot, L. and Von Zelewsky, A., "Cyclometalated Complexes of Platinum (II): Homoleptic Compounds with Aromatic C, N Ligands," Inorg. Chem. (1987), 26, 2814-2818.
Cocchi, M. et al., "Highly efficient organic electroluminescent devices based on cyclometallated platinum complexes as new phosphorent emitters," Synthetic Metals, 147, 253-256, (2004).
Cocchi, M. et al., "Highly efficient organic electroluminescent light-emitting diodes with a reduced quantum efficiency roll off at large current densities," Applied Physics Letters, 84, 7, 1052-1054 (2004).
Davison, A. et al., "Further Examples of Complexes Related by Electron-Transfer Reactions: Complexes Derived from Bis9trifluoromethyl)-1,2-dithietene," Inorg. Chem. (1964) 3/6 p. 814.
Denmark, S. et al., "Cyclopropanation with Diazomethane and Bis(Oxazoline) Palladium (II) Complexes," Journal of Organic Chemistry, 62, No. 10, May 16, 1997.
Doucet, et al., "Palladium-Based Catalytic Systems for the Synthesis of Conjugated Enynes by Sonogashira Reactions and Related Alkynylations," Angew. Chem. Int. Ed. (2007) 46, 834.
Gareau, Y. et al. "Free Radical Reaction of Diisopropyl Xanthogen Disulfide with Unsaturated Systems," Heterocycles (1998) 48, p. 2003.
Gebauer, T. et al., "Mesoionic bora-tetraazapentalenes—fully reversible two step redox systems," Chemical Communications (2004), (16), 1860-1861.
Huang et al., "Synthesis of Perfluoro-2-alkynenitriles," Tetrahedron Letters (1981) 22, p. 5283. Krebs et al., "Strained Cyclic Acetylenes, VII Addition of Sulfur and Pyridine-N-Oxide to Seven Membered Cycloalkynes," Heterocycles (1979) 12, p. 1153.
Krespan, C.G.; "Bis-(polyfluoroalkyl)-acetylenes. IV. Fluorinated Dithietenes and Related Heterocyclic Compounds From Bis-(polyfluoroalkyl)-acetylenes and Sulfur," J.Am. Chem. Soc. (1961) 83, 3434.
Lo, K. M., et al., "Synthesis and spectroscopic studies of thienyl triorganotin (IV) compounds," J. Organometal. Chem. (1992), 430, 149.
Marder et al., "Synthesis, Optical Properties, Crystal Stuctures and Phase Behavior of Selectively Fluorinated 1,4-bis(4'-pyridylethynyl)benzenes, 4-(phenylethynyl)pyridines and 9,10-bis(4'-pyridylethynyl)-anthracene, and a $Zn(NO_3)_2$ Coordination Polymer," J. Mater. Chem. (2004) 14, 2395.
Mayer, R., et al. "Synthese der 1,3-Dithiol-2-thione," Angew. Chem. (1964) 76, p. 143.
Nakayama, J. et al., "A Convenient Synthesis of 1,2-Dithietes and 1,2-Dithioxo Compounds Stabilized by Buttressing and Resonance Effects, Respectively, by Sulfuration of Alkynes with Elemental Sulfur," Bull. Chem. Soc. Jpn. (1993) 66, p. 623.

(Continued)

*Primary Examiner* — Harold Pyon
*Assistant Examiner* — Timothy Chiang
(74) *Attorney, Agent, or Firm* — Sutherland Asbill & Brennan LLP

(57) ABSTRACT

The present invention relates to square planar transition metal complexes and their use in organic semiconductive materials as well as in electronic or optoelectronic components.

13 Claims, No Drawings

OTHER PUBLICATIONS

Okada, S. et al. "Substituent effects of iridium complexes for highly efficient red OLEDs," Dalton Trans., 2005, 1583.

Pereira, R. P. et al., "Electrosynthesis and characterization of polypyrrole doped with [Bi(dmit)2]<->," Synthetic Metals, Apr. 20, 2005, p. 21-26.

Pfeiffer, M. et al., "Controlled doping of phthalocyanine layers by cosublimation with acceptor molecules: A systematic Seebeck and conductivity study," Applied Physics Letters, vol. 73, No. 22 Nov. 20, 1998, pp. 3202-3204.

Schrauzer, et al. "Preparation, Reactions, and Structure of Bisdithio-α-diketone Complexes of Nickel, Palladium, and Platinum," J. Am. Chem. Soc. (1965) 87/7 1483-9.

Schrauzer, et al., "Reaktionen von Ubergangsmetallsulfiden mit Alkinen. Zur Kenntnis von Metallkomplexen der α-β-Dithiodiketone," Z. Naturforschg. (1964) 19b, 192-8.

Shinar, J. "Organic Light-Emitting Devices—A Survey," AIP-Press, Springer, New York 2004.

Sonogahsira, et al., "A Convenient Synthesis of Acetylenes: Catalytic Substitutions of Acetylenic Hydrogen with Bromoalkenes, Iodoarenes, and Bromopyridines." Tetrahedron Letters (1975) 50, 4467.

Sotoyama, W. et al. "Efficient organic light-emitting diodes with phosphorescent platinum complexes containing N-C-N-coordinating tridentate ligand," Appl. Phys. Lett. 2005, 86, 153505.

Taguchi, et al., "Comparison of p-type and n-type organic field-effect transistors using nickel coordination compounds," Chemical Physics Letters, Apr. 15, 2006, p. 395-398.

Tang, C.W. et al., "Organic electroluminescent diodes," Applied Physics Letters, vol. 51, No. 12, Sep. 21, 1987, pp. 913-915.

Tarraga, A. et al., "Synthesis and electrochemical study of novel and oxazolo-ferrocene derivatives displaying redox-switchable character," Tetrahedron, 57, 31, Jul. 30, 2001, pp. 6765-6774.

Tung, Y. L. et al. "Organic light-emitting diodes based on charge-neutral Os(II) emitters: generation of saturated red emission with very high external quantum efficiency," J. Mater. Chem., 2005, 15, 460-464.

Yang, X. H. et al. "Polymer electrophosphorescence devices with high power conversion efficiencies," Appl. Phys. Lett. 2004, 84, 2476.

Yersin, H. and Donges, D. "Low-Lying Electronic States and Photophysical Properties of Organometallic Pd(II) and Pt(II) Compounds. Modern Research Trends Presented in Detailed Case Studies," Topics in Curr. Chem. (2001), 214, 81.

Yersin, H. "Highly Efficient OLEDs with Phosphorescent Materials," Wiley-VCH 2006.

International Search Report, International App. No. PCT/EP2007/006683, Nov. 13, 2007.

International Search Report, International App. No. PCT/EP2007/004638, Jul. 23, 2007.

International Search Report, International App. No. PCT/DE2006/002330, Apr. 24, 2007.

International Search Report, International App. No. PCT/DE2007/000587, Sep. 11, 2007.

Disclosure Under 37 C.F.R. 1.56 for U.S. Appl. No. 12/429,034 (Submitted Herewith).

Kondoh, A. et al. "Copper-catalyzed anti-hydrophosphination reaction of 1-alkynylphosphines with diphenylphosphine providing (Z)-1,2-diphosphino-1-alkenes," J. Am. Chem. Soc. 2007, 129, pp. 4099-4104.

Yang, C. et al. "Third-order nonlinear optical properties of new square planar complexes with donor-metal-acceptor structure," Synthetic Metals (2001), 121 (1-3), 1491-1492 (Abstract Only).

Kamenicek, J. et al. "Cobalt and nickel complexes with maleonitriledithiolate and selected N,P-ligands," Acta Universitatis Palackianae Olomucensis, Facultas Rerum Naturalium, Chemica (2002), 41, pp. 17-25 (Abstract Only).

German Search Report for Application No. 10 2008 051 737.2, Aug. 3, 2009.

* cited by examiner

SQUARE PLANAR TRANSITION METAL COMPLEXES AND ORGANIC SEMICONDUCTIVE MATERIALS USING THEM AS WELL AS ELECTRONIC OR OPTOELECTRIC COMPONENTS

CROSS REFERENCES TO RELATED APPLICATIONS

Applicants hereby claim priority under 35 U.S.C. 119(e) to U.S. Patent Application No. 61/105,842, filed Oct. 16, 2008, the disclosure of which is expressly incorporated herein by reference in its entirety.

FIELD OF INVENTION

The present invention relates to square planar transition metal complexes, organic semiconductive materials as well as electronic or optoelectric components.

BACKGROUND OF INVENTION

It is known that organic semiconductors can be chanced as regards their electrical properties, especially their electrical conductivity, as is also the case with inorganic semiconductors such as silicon semiconductors. An elevation of the conductivity, which is rather low at first, is achieved here by the producing of charge carriers in the matrix material, as well as a change in the Fermi level of the semiconductor according to the type of the used dopant. A doping results here in an elevation of the conductivity of the charge transport layers, which reduces ohmic losses, and in an improved transfer of the charge carriers between contacts and organic layer.

Inorganic dopants such as alkali metals (e.g., cesium) or Lewis acids (e.g., FeCl3) are mostly disadvantageous in organic matrix material on account of their high coefficients of diffusion, since the function and stability of the electronic components is adversely affected. Furthermore, the release of dopants via chemical reactions into the semiconductive matrix material in order to make dopants available is known. However, the reduction potential of such released dopants is often not sufficient for various instances of application such as, in particular, for organic light-emitting diodes (OLED). Furthermore, further compounds and/or atoms, for example, atomic hydrogen, are produced in the release of the dopants, which affects the properties of the doped layer and of the corresponding electronic component.

The acceptor-like material can also be used as hole injection layer. Thus, for example, a layered structure anode/acceptor/hole transporter can be produced. The hole transporter can be a pure layer or a mixed layer. In particular, the hole transporter can also be doped with an acceptor. The anode can be ITO, for example. The acceptor layer can be 0.5-100 nm thick, for example. In one embodiment the acceptor layer can be doped with a donor-like molecule.

Square planar transition metal complexes are known, for example from the WO 2005/123754 A2, that can be used in a great plurality of electronic applications, for example, inactive electronic components, passive electronic components, in electroluminescence devices (e.g., organic light-emitting diodes), photovoltaic cells, light-emitting diodes, field effect transistors, photo transistors, etc.) The use of the described square planar transition metal complexes is indicated as charge transport material.

The present invention has the objective of making novel square planar transition metal complexes in which their use results in improved organic semiconductor matrix materials, charge injection layers, electrode materials and storage materials, in particular in electronic or optoelectronic components, in comparison to the state of the art. In particular, the transition metal complexes should have sufficiently high reduction potentials, not have disturbing influences on the matrix material, and make available an effective elevation of the charge carrier number in the matrix material, and be able to be handled in a comparatively simple manner.

Further objectives of the present invention reside in making available organic semiconductive materials and electronic components or optoelectronic components as well as in making available possibilities for using the transition metal complexes.

BRIEF SUMMARY

The objective of the invention is achieved by:
a) a square planar transition metal complex according to any one of the following formulas (I) or (II):

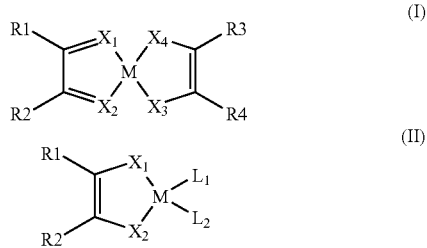

in which M is a transition metal selected from the groups 8 to 12 of the periodic system of the elements, X1, X2, X3 and X4 are independently selected from S, Se, NR5 and PR5, in which R5 is selected from, substituted or unsubstuted, linear or branched alkyl, cycloalkyl, aryl, heteroaryl, condensed aromatic rings, donor groups and acceptor groups, R1 and R2 are different from one another and/or R3 and R4 are different from one another, wherein R1, R2, R3 and R4 are otherwise independently selected from simply or multiply halogenated, fluorinated, aromatic structures and/or heteroaromatic structures, simply or multiply cyanated aromatic and heteroaromatic structures, cyanated halogen aromatics and halogen heteroaromatics, halogenated, preferably fluorinated, aliphatic, linear or branched, and cyclic hydrocarbons, cyano, and halogenated, preferably fluorinated, aliphatic nitrile compounds, L1 and L2 are independently selected from alkylated and/or aromatic amine, alkylated and/or aromatic phosphine, halogen, pseudohalogen, NCS, SCN and CN.

b) a square planar transition metal complex with the formula (I) or (II) where R1 and R4 are identical and/or R2 and R3 are identical.

c) a square planar transition metal complex with the formula (I) or (II) where R1 and R4 are identical as well as are either H or CN, or R2 and R3 are identical as well as are either H or CN.

d) a square planar transition metal complex with the formula (I) or (II) where M is selected from nickel, copper, gold, palladium, platinum, iron, cobalt, preferably nickel, palladium, platinum, cobalt and iron.

e) a square planar transition metal complex where R1, R2, R3 and R4 are independently selected from perfluorinated and perchlorinated aromatics and heteroaromatics, especially pentafluorophenyl and tetrafluoropyridine.

f) an organic semiconductive material containing an organic matrix compound and a square planar transition metal complex.
g) an electrically doped organic semiconductive material according were the molar doping ratio of dopant to matrix molecule or the doping ratio of dopant to monomeric units of a polymeric matrix molecule is between 20:1 and 1:100,000, preferably 10:1 and 1:1,000, especially preferably 1:1 and 1:100.
h) an electronic or optoelectronic component with an electronically functionally active area using the compounds (I) and/or (II).
i) an electronic or optoelectronic component where the electronically active area comprises an organic semiconductive matrix material that is doped with at least one dopant in order to change the electronic properties of the semiconductive matrix material and that the dopant is a transition metal complex.
j) an electronic or optoelectronic component in the form of an organic light-emitting diode, a photovoltaic cell, an organic solar cell, an organic diode or an organic field effect transistor.
k) the use of a square planar transition metal complex with formula (I) ir (II) as dopant for doping an organic semiconductive matrix material, as charge injection layer, as electrode material or as storage material in electronic or optoelectronic components.

ADVANTAGEOUS EFFECTS OF THE INVENTION

The first objective is solved by a square planar transition metal complex according to any one of the following formulas (I) or (II):

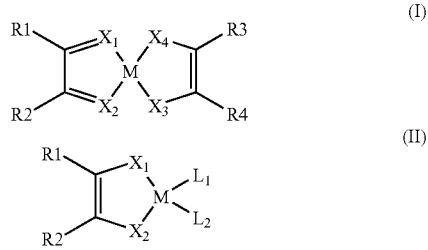

in which M is a transition metal selected from the groups 8 to 12 of the periodic system of the elements, $X_1$, $X_2$, $X_3$ and $X_4$ are independently selected from S, Se, $NR_5$, and $PR_5$, in which $R_5$ is selected from, substituted or unsubstuted, linear or branched alkyl, cycloalkyl, aryl, heteroaryl, condensed aromatic rings, donor groups and acceptor groups, $R_1$ and $R_2$ are different from one another and/or $R_3$ and $R_4$ are different from one another, wherein, $R_1$, $R_2$, $R_3$ and $R_4$ are otherwise independently selected from singly or multiply halogenated, preferably fluorinated, aromatic structures and/or heteroaromatic structures, singly or multiply cyanated aromatic and heteroaromatic structures, cyanated halogen aromatics and halogen heteroaromatics, halogenated, preferably fluorinated, aliphatic, linear or branched, and cyclic hydrocarbons, cyano, and halogenated, preferably fluorinated, aliphatic nitrite compounds, $L_1$ and $L_2$ are independently selected from alkylated and/or aromatic amine, alkylated and/or aromatic phosphine, halogen, pseudohalogen, NCS, SCN and CN. The further tasks are solved by an organic semiconductive material containing a metal complex of formula (I) or (II), as well as by an electronic or optoelectronic component containing a metal complex of formula (I) or (II), as well as by the use of a square planar transition metal complex according to formula (I) or (II) as dopant for doping an organic semiconductive matrix material, as charge injection layer, as electrode material or as storage material in electronic or optoelectronic components. Further preferred embodiments result from the subclaims.

A significant feature of the square planar transition metal complexes in accordance with the invention is their asymmetry, that is, that the substituents R1 and R2 on the one side and/or the substituents R3 and R4 on the other side are different from each other. This leads to especially good results regarding the conductivity and the ability to use the complexes in organic semiconductive material and the like.

It was surprisingly determined that when using the disclosed novel transition metal complexes in accordance with the invention a substantially stronger and/or more stable dopant is present than in the case of previously known acceptor compounds, which square planar transition metal complexes are used here in neutral form as a p-dopant in relation to an organic semiconductive matrix material. In particular, the conductivity of charge transport layers is significantly raised when using the complexes, and/or the transition of the charge carriers between the contacts and organic layer for electronic components is significantly improved. Without being limited by this assumption, it is assumed that, when using the disclosed transition metal complexes in a doped layer, CT complexes are formed, in particular by the transfer of at least one electron from the particular surrounding matrix material. In this manner the matrix material gains a conductivity that is greater in comparison to the conductivity of the undoped matrix material. Conductivities of undoped matrix materials are as a rule <10-8 s/cm, in particular frequently <10-10 s/cm. Care is to be taken here that the matrix materials have a sufficiently high purity. Such purities can be achieved with traditional methods, for example, gradient sublimation. With doping, the conductivity of such matrix material can be raised to greater than <10-8 s/cm, frequently >10-5. This applies in particular to matrix materials that have an oxidation potential greater than −0.5 V vs. Fc/Fc+, preferably greater than 0 V vs. Fc/Fc+, in particular greater than +0.2 V vs. <Fc/Fc+. The indication Fc/Fc+ refers to the redox pair ferrocene/ferrocenium, that is used as reference in an electrochemical determination of potential, for example, in cyclovoltammetry.

The asymmetric transition metal complexes in accordance with the invention have, compared to the symmetric analogues, a distinctly poorer tendency to crystallization, so that it becomes easier for it to remain in the amorphous phases customary for inorganic semiconductors produced during the vapor deposition process.

It was furthermore determined that the herein described square planar transition metal complexes can also be used as injection layer in electronic components, preferably between an electrode and a semiconductor layer, that can also be doped, or also as blocker layer, preferably between emitter- and transport layer in electronic components. The use in accordance with the invention makes possible a photo- or light-induced irreversible doping of organic semiconductors. In the use in accordance with the invention the described complex compounds are preferably isolated molecules that therefore are preferably present in the particular semiconductive layer as isolated molecules that are not fixed by chemical bonds to each other and/or to a matrix or to another component. The complexes in accordance with the invention have a surprisingly high stability regarding their reactivity with the atmosphere.

DETAILED DESCRIPTION

Preparation of Planer Transition Metal Complexes

Square planar transition metal complexes can be synthesized according to known processes and are also partly commercially obtainable. The synthesis of such compounds is described, for example, in the following literature passages that are included herewith in the application to their full extent as reference. It is understood that the cited literature passages are indicated only by way of example. According to Schrauzer et al. such transition metal complexes can be prepared from 1,2-diketones or 2-hydroxyketones, phosphorus pentasufide and a suitable transition metal salt, J. Am. Chem. Soc. (1965) 87/7 1483-9. The conversion of transition metal carbonyls with sulfur and acetylenes also results in the complexes in accordance with the invention, A. Davison et al. Inorg. Chem. (1964) 3/6 814. Instead of the transition metal carbonyls even other formally 0-valent transition metal compounds such as, for example, appropriate cyclooctadienyls, phosphines, etc., but also pure transition metals can be used, G. N. Schrauzer et al. Z. Naturforschg. (1964) 19b, 192-8.

Preparation of Planar Transition Metal Complexes

The corresponding asymmetric acetylenes can be prepared, for example, via a Sonogashira coupling (Sonogashira, Tetrahedron Letters (1975) 50 4467; Doucet, Hierso, Angew. Chem. Int. Ed. (2007) 46 834, via a modified Wittig reaction (Huang, Shen, Ding, Zheng, Tetrahedron Letters (1981) 22 5283) or with butyllithium (Marder et al., J. Mater. Chem. (2004) 14 2395 and subsequently reacted with sulfur and nickel-(0) compounds or metallic nickel to the corresponding nickel bisethylene dithiolates, (Krespan, J. Am. Chem. Soc. (1961) 83 3434; Krebs et al, Heterocycles (1979) 12 1153).

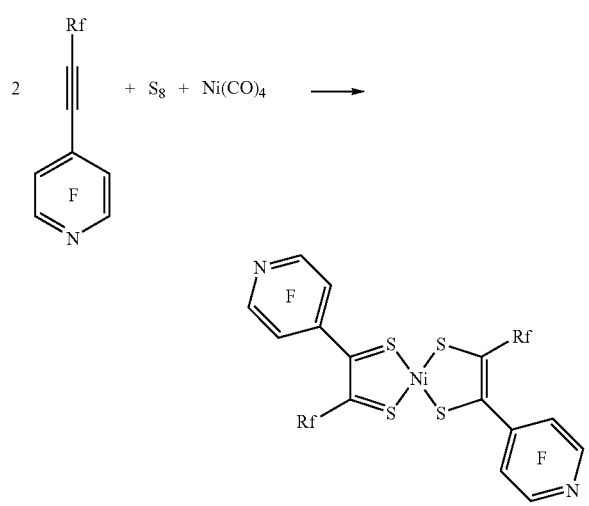

Moreover, the acetylenes can be reacted with sulfur to dithiet- and dithione compounds that can then be reacted for their part with nickel-(0)-compounds or metallic nickel to the corresponding nickel bisethylene dithiolates. Here, Nickel is used in all schemes to represent all claimed transition metals.

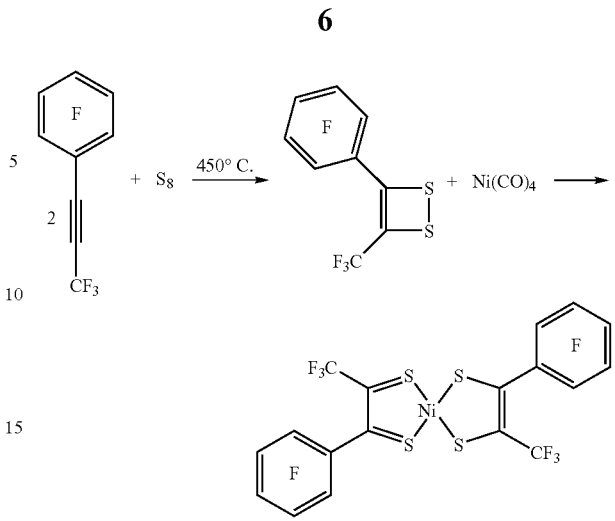

Further variants for converting acetylenes into dithiets made use of carbon disulfide partially in the present of sulfur or disulfurdichloride usually in polar solvents, often also at elevated temperature and elevated pressure, (Nakayama et al, Bull. Chem Soc. Jpn., (1993) 66 623; Krebs et al., Heterocycles (1979) 12 1153; Mayer et al., Angew. Chem. (1964) 76 143). A further possibility of synthesis for transition metal dithiolates is via 1,3-dithiole-2-ones, that can be prepared from acetylenes and diisopropylxanthogenedisulfide in the presence of azoisobutyronitrile (AIBN) (Gareau, Beauchemin, Heterocycles (1998) 48 2003).

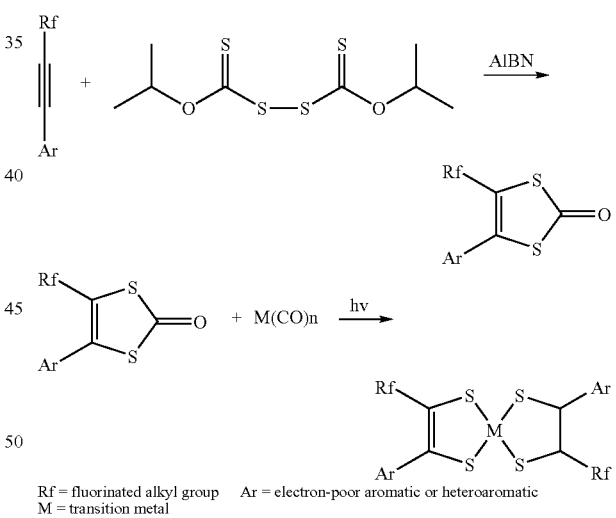

Rf = fluorinated alkyl group    Ar = electron-poor aromatic or heteroaromatic
M = transition metal Doping Among others, phthalocyanine complexes, for example, Zn (ZnPc), Cu (CuPc), Ni (NiPc) or other metals can be used as p-dopable matrix materials and the phthalocyanine ligand can also be substituted. Also other metallic complexes of naphtocyanines and porphyrines can be optionally used. Furthermore, also arylated or heteroarylated amines and benzidine derivatives can be used as matrix material that can be substituted or non-substituted, especially also spiro-linked ones, for example, TPD, a-NPD, TDATA, Spiro-TTB. In particular, a-NPD and SpiroTTB can be used as matrix material.

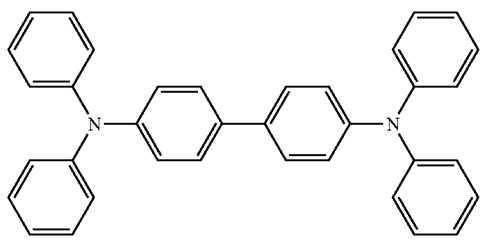

TPD

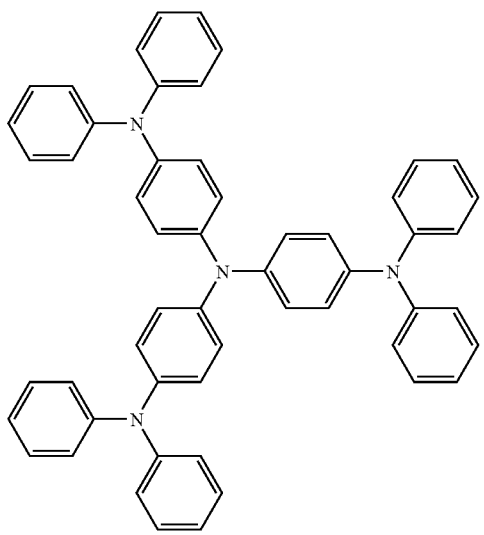

TDATA

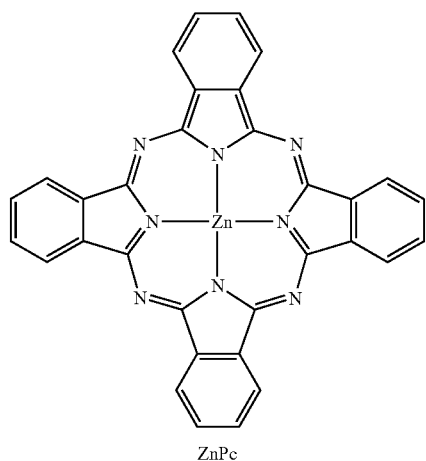

ZnPc

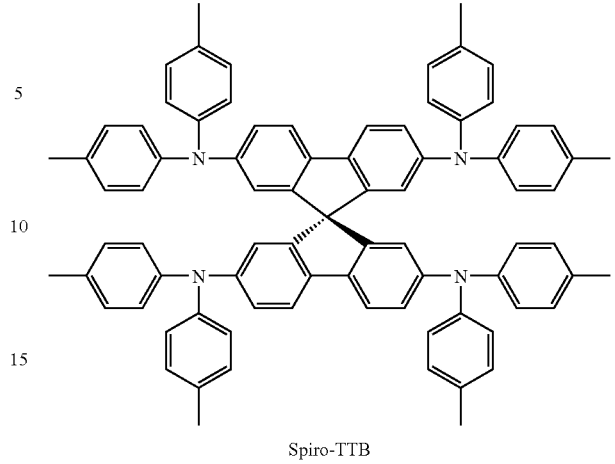

Spiro-TTB

In addition to polyaromatic hydrocarbons, heteroaromatic compounds such as especially imidazole, thiophene, thiazole derivatives, heterotriphenylenes or also others can be used as matrix material, optionally also heteroaromatic dimeric, oligomeric or polymeric compounds. The heteroaromatic compounds are preferably substituted, especially aryl-substituted, for example, phenyl- or naphthyl-substituted. They can also be present as Spiro compounds.

It is understood that the named matrix materials can also be used mixed with each other or with other materials within the scope of the invention. It is understood that even other suitable organic matrix materials can be used that have semiconductive properties.

Doping Concentration

The dopant is preferably present in the doping concentration of <1:1 to the matrix molecule or to the monomeric unit of a polymeric matrix molecule, such as in a doping concentration of 1:2 or less, especially preferably 1:5 or less or 1:10 or less. The doping concentration can be in the range of 20:1 to 1:100,000, in particular in the range of 10:1 to 1:1000, preferably in the range of 1:1 to 1:100, without being limited to them.

Carrying Out of the Doping

The doping of the particular matrix material with the compounds in accordance with the invention can take place by one or a combination of the following processes:
a) Mixed evaporation in the vacuum with a source for the matrix material and one for the dopant.
b) Sequential depositing of the matrix material and of the p-dopant on a substrate with subsequent inward diffusion of the dopant, in particular by thermal treatment.
c) Doping of a matrix layer by a solution of p-dopant with subsequent evaporation of the solvent, in particular by thermal treatment.
d) Surface doping of a matrix material layer by a layer of dopant applied on the surface.
e) Preparation of a solution of matrix molecules and dopant and subsequent preparation of a layer of this solution by conventional methods such as, for example, evaporation of the solvent or spin-coating.

Thus, p-doped layers of organic semiconductors can be prepared in this manner that can be used in multiple ways.

Semiconductive Layer

Semiconductive layers can be produced by the electron-poor transition metal complex compounds in accordance with the invention that are optionally formed rather linearly such as, e.g., conductivity paths, contacts or the like. The p-dopants transition metal complexes can be used together with another compound that can work as a matrix material, where the doping ratio can be 1:1 or smaller. The dopant used can also be present in higher portions relative to the other molecule or compound, so that the ratio dopant:compound can be in the ratio >1:1 e.g., in the ratio $\geq$2:1, $\geq$5:1, $\geq$10:1 or $\geq$20:1 or higher. The particular other component can be one that can be used as matrix material in the case of the production of doped layers, without being limited to this. If necessary, the dopant used can also be present in substantially pure form, for example, as pure layer.

The area containing a dopant or consisting substantially or completely of it can be contacted in an electrically current-conducting manner in particular by an organic semiconductive material and/or an inorganic semiconductive material, for example, arranged on such a substrate.

The mentioned electron-poor transition metal complex compounds are preferably used in accordance with the invention as p-dopants, e.g., in a ratio of $\leq$1:1 or $\leq$1:2. Semiconductive layers with conductivities at room temperature in the range of 10-5 s/cm or higher can be achieved, for example, of 10-3 s/cm or higher, for example of 10-1 s/cm by means of the electron-poor compounds used in accordance with the invention as p-dopants, for example, when using ZnPc, Spiro-TTB or a-NPD as matrix. When using zinc phthalocyanine as matrix a conductivity of greater than 10-8 s/cm was achieved, for example, 10-6 s/cm. It was previously not possible to dope this matrix with organic acceptors since the reduction potential of the matrix is too low. In contrast thereto, the conductivity of undoped zinc phthalocyanine is maximally 10-10 s/cm.

It is understood that the layer or the structure with the dopants can contain one or more different such electron-poor transition metal complex compounds.

Electronic Component

A plurality of electronic components or equipment containing them can be produced with a p-doped organic semiconductor layer using the described compounds for producing p-doped organic semiconductor materials that can be arranged in particular in the form of layers or electric wiring paths. In the sense of the invention the concept "electronic components" also comprises optoelectronic components. The electronic properties of an area of the component that is electronically functionally active such as its electrical conductivity, light-emitting properties or the like, can be advantageously changed by the described novel compounds. Thus, the conductivity of the doped layers can be improved and/or the improvement of the charge carrier injection of contacts into the doped layer can be achieved.

The invention comprises in particular organic light-emitting diodes (OLED), organic solar cells, field effect transistors, organic diodes, in particular those with high rectification ratio such as 103-107, preferably 104-107 or 105-107, and organic field effect transistors produced by the electron-poor transition metal complex compounds.

A p-doped layer based on an organic matrix material can be present in the electronic component in the following layer structures, in which the base materials or matrix materials of the individual layers are preferably organic:

p-i-M: p-doped semiconductor-insulator-metal,
M-i-p: metal-insulator-p-doped semiconductor,
p-i-n: p-doped semiconductor-insulator-n-doped semiconductor,
n-i-p: n-doped semiconductor-insulator-p-doped semiconductor.

"i" is again a undoped (intrinsic) layer, "p" is a p-doped layer.

The contact materials are hole-injecting here, in which case on the p-side, for example, a layer or a contact of ITO or Au can be provided, or electron-injecting, in which case on the n-side a layer or a contact of ITO, Al or Ag can be provided.

In the above structures even the i-layer can be omitted if required, as a result of which layer sequences with p-n or n-p transitions can be obtained.

The use of the described compounds is, however, not limited to the above-named exemplary embodiments; in particular, the layer structures can be supplemented or modified by the introduction of additional suitable layers. In particular, OLEDs with such layer sequences, especially with pin—or with a structure inverse to it, can fabricated with the described compounds.

In particular, organic diodes of the type metal-insulator-p-doped semiconductors (min) or also, optionally of the pin-type, for example on the basis of zinc phthalocyanine, can be produced with the aid of the described p-dopants. These diodes show a rectification ratio of 105 and higher. Furthermore, electronic components with p-n transitions can be produced using the dopants in accordance with the invention, in which case the same semiconductor material is used for the p- and the n-doped side (p-n-homojunction), wherein a described electron-poor transition metal complex compound is used for the p-doped semiconductor material.

The electron-poor transition metal complex compounds can be used in accordance with the invention in the electronic components but also in layers, conductivity paths, point contacts or the like if they predominate in contrast to another component, for example, as injection layer in pure or in substantially pure form.

Further tasks and advantages of the present invention will now be described in a clear manner using the following examples that are to be considered solely as illustrative and not as limiting the scope of the invention.

EXAMPLES OF APPLICATION

An extremely electron-poor transition metal complex compound is prepared in a very clean manner.

The proposed electron-poor transition metal complex compound is evaporated at the same time with the matrix material. According to the exemplary embodiment the matrix material is zinc phthalocyanine, spiro-TTB or a-NDP. The p-dopant and the matrix material can be evaporated in such a manner that the layer precipitated on the substrate in a vacuum evaporation system has a doping ratio of p-dopant to matrix material of 1:10.

The particular layer of the organic semiconductor material doped with the p-dopant is applied on an ITO layer (indium tin oxide) arranged on a glass substrate. After the application of the p-doped organic semiconductor layer a metal cathode is applied, for example, by vapor-depositing a suitable metal on it in order to produce an organic light-emitting diode. It is understood that the organic light-emitting diode can also have a so-called inverted layer construction in which the layer sequence is: Glass substrate—metal cathode p-doped organic layer—transparent conductive cover layer (for example, ITO). It is understood that further layers can be provided between the individual named layers depending on the application.

SPECIFIC EXAMPLES

EX1

EX2

EX3

EX4

EX5

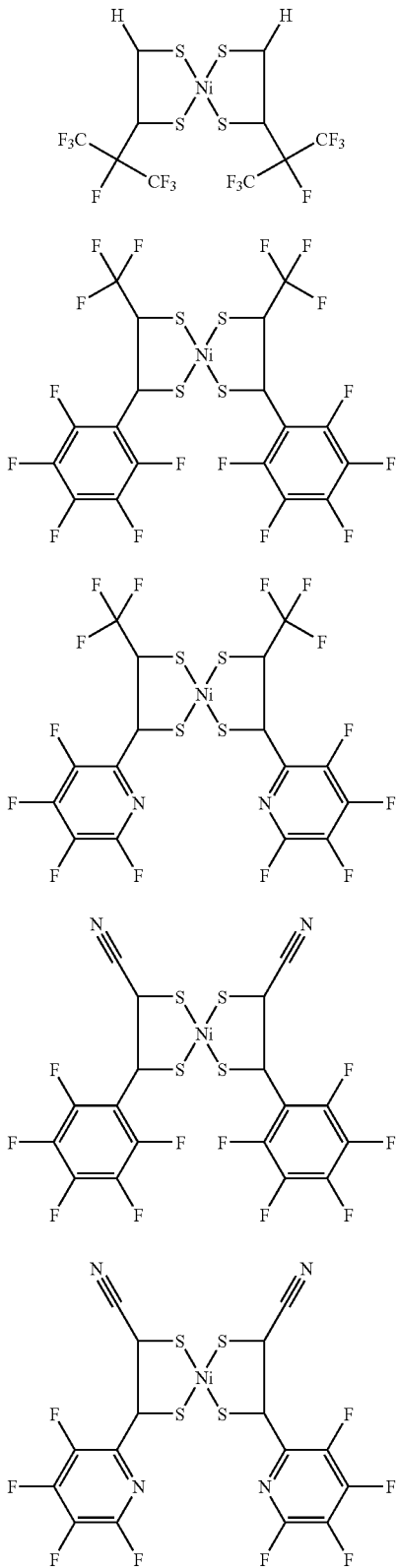

EXAMPLE

The nickel complex EX1 was synthesized according to the procedure below:

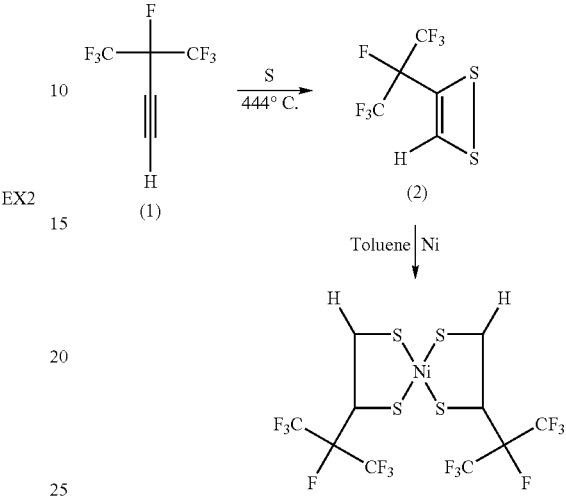

The compound (1) passed as Vapour (or gas) trough boiling sulfur to obtain compound (2), which is used as raw material, without further purification. Compound (2) was reacted with RANEY Nickel in toluene solution to obtain the final compound. This was purified by column chromatography (MPLC) on silica with hexane as eluent. The mass spectra analysis shows a very clear peak at m/z=574.

Conductivity Example

The neutral nickel complex EX1 was used for the doping of spiro-TTB as matrix material. Doped layers with a doping concentration of 5 wt % of dopant:matrix material produced by dissolving the materials in CH2Cl2. The materials have a good solubility and the solution looks dark purple. The solution was deposited over a glass substrate comprising ITO electrodes with spin-coating at 1000 rpm for 30 seconds.

The film was dryied at 110° C. for 10 minutes.

The conductivity of such a film is about 5×10-5 S/cm, which is much higher than the conductivity of non-doped Sprio-TTB, which is lower than 5×10-8 S/cm.

The features disclosed in the description and the claims can be significant individually as well as in any combination for the realization of the invention and its very different embodiments.

OLED Example

An OLED was constructed using a spin coated doped HTL as in the example above with a thickness of 120 nm, except that the ITO layer over the glass substrate was had a larger surface. The substrate was transferred to vacuum and the following layers were deposited by thermal evaporation:

| Material | Layer thickness (nm) |
| --- | --- |
| Spiro-TTB | 20 |
| Alq3 doped with DCJTB (5 mol %) | 20 |
| TTPP | 5 |
| TTPP doped with W2hpp (4 mol %) | 40 |
| Al | 100 |

Here DCJTB is the a red fluorescent emitter dopant 4-(Di-cyanomethylene)-2-tert-butyl-6-(1,1,7,7-tetramethyljulolidin-4-yl-vinyl)-4H-pyran. Alq3 is Tris(8-hydroxyquinolinato)aluminum, a conventional emitter host. TTPP is 2,4,7,9-tetraphenyl-1,10-phenanthroline, an electron transport material. W2hpp is Tetrakis(1,3,4,6,7,8-Hexahydro-2H-pyrimido[1,2-a]pyrimidinato)ditungsten (II), a typical organic n-dopant.

The OLED showed good performance with voltage onset at around 3 V, and a high brightness at 5 V.

The invention claimed is:

1. A square planar transition metal complex, wherein the metal complex comprises a compound of one of the following formulas (I) or (II):

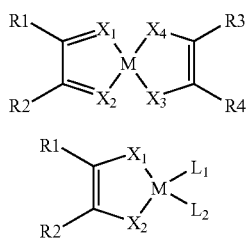

wherein M is a transition metal selected from the groups 8 to 12 of the periodic system of the elements;

$X_1$, $X_2$, $X_3$, and $X_4$ are independently selected from S, Se, NR5, and PR5, wherein R5 is selected from the group consisting of, substituted or unsubstituted, linear or branched alkyl, cycloalkyl, aryl, heteroaryl, condensed aromatic rings, donor groups, and acceptor groups;

R1 and R2 are different from one another and/or R3 and R4 are different from one another, wherein R1, R2, R3 and R4 are otherwise independently selected from the group consisting of singly or multiply halogenated aromatic structures, singly or multiply halogenated heteroaromatic structures, singly or multiply cyanated aromatic structures, singly or multiply cyanated heteroaromatic structures, cyanated halogen aromatics, cyanated halogen heteroaromatics, halogenated hydrocarbons, cyano, and halogenated aliphatic nitrile compounds, wherein the halogenated hydrocarbons are aliphatic, linear, branched, or cyclic; and L1 and L2 are independently selected from the group consisting of alkylated amine, aromatic amine, alkylated phosphine, aromatic phosphine, halogen, pseudohalogen, NCS, SCN, and CN.

2. The square planar transition metal complex according to claim 1, wherein R1 and R4 are identical, or R2 and R3 are identical.

3. The square planar transition metal complex according to claim 2, wherein R1 and R4 are H or CN, or R2 and R3 are H or CN.

4. The square planar transition metal complex according to claim 1, wherein M is selected from the group consisting of nickel, copper, gold, palladium, platinum, iron, and cobalt.

5. The square planar transition metal complex according to claim 1, wherein R1, R2, R3, and R4 are independently selected from perfluorinated aromatics, perchlorinated aromatics, perfluorinated heteroaromatics, and perchlorinated heteroaromatics.

6. An organic semiconductive material, wherein the organic semiconductive material comprises an organic matrix compound and a square planar transition metal complex, wherein the metal complex comprises a compound of formulas (I) or (II):

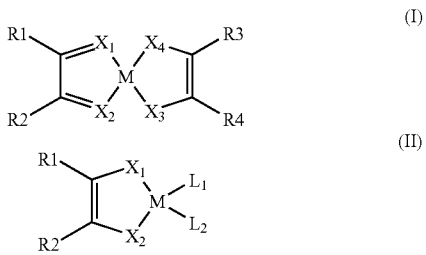

wherein M is a transition metal selected from the groups 8 to 12 of the periodic system of the elements;

$X_1$, $X_2$, $X_3$, and $X_4$ are independently selected from S, Se, NR5, and PR5, in which R5 is selected from the group consisting of, substituted or unsubstituted, linear or branched alkyl, cycloalkyl, aryl, heteroaryl, condensed aromatic rings, donor groups and acceptor groups;

R1 and R2 are different from one another and/or R3 and R4 are different from one another, wherein R1, R2, R3 and R4 are otherwise independently selected from the group consisting of singly or multiply halogenated aromatic structures, singly or multiply halogenated heteroaromatic structures, singly or multiply cyanated aromatic structures, singly or multiply halogenated heteroaromatic structures, cyanated halogen aromatics cyanated halogen heteroaromatics, halogenated hydrocarbons, cyano, and halogenated aliphatic nitrile compounds, wherein the halogenated hydrocarbons are aliphatic, linear, branched, or cyclic; and L1 and L2 are independently selected from the group consisting of alkylated amine, aromatic amine, alkylated phosphine, aromatic phosphine, halogen, pseudohalogen, NCS, SCN, and CN.

7. The organic semiconductive material according to claim 6, wherein the molar doping ratio of dopant to matrix molecule or the doping ratio of dopant to monomeric units of a polymeric matrix molecule is between 20:1 and 1:100,000.

8. An electronic or optoelectronic component, wherein the component comprises an electronically functionally active area, wherein the electronically active area comprises at least one transition metal complex, wherein the at least one transition metal complex is a metal complex comprising a compound of formulas (I) or (II):

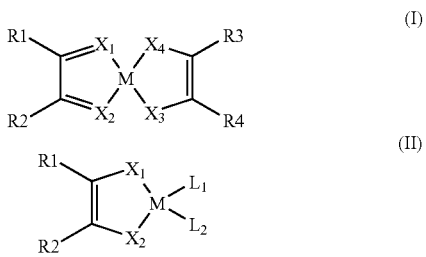

wherein M is a transition metal selected from the groups 8 to 12 of the periodic system of the elements;

$X_1$, $X_2$, $X_3$, and $X_4$ are independently selected from S, Se, NR5, and PR5, in which R5 is selected from the group consisting of, substituted or unsubstituted, linear or branched alkyl, cycloalkyl, aryl, heteroaryl, condensed aromatic rings, donor groups, and acceptor groups;

R1 and R2 are different from one another and/or R3 and, R4 are different from one another, wherein R1, R2, R3 and R4 are otherwise independently selected from the group consisting of singly or multiply halogenated aromatic structures, singly or multiply halogenated heteroaromatic structures, singly or multiply cyanated aromatic structures, singly or multiply cyanated heteroaromatic structures, cyanated halogen aromatics, cyanated halogen heteroaromatics, halogenated hydrocarbons, cyano, and halogenated aliphatic nitrile compounds, wherein the halogenated hydrocarbons are aliphatic, linear, branched, or cyclic; and L1 and L2 are independently selected from the group consisting of alkylated amine, aromatic amine, alkylated phosphine, aromatic phosphine, halogen, pseudohalogen, NCS, SCN, and CN.

9. The electronic or optoelectronic component according to claim 8, wherein the electronically active area comprises an organic semiconductive matrix material that is doped with at least one dopant in order to change the electronic properties of the semiconductive matrix material, and wherein the dopant is the square planar transition metal complex.

10. The electronic or optoelectronic component according to claim 8, wherein the component comprises an organic light-emitting diode, a photovoltaic cell, an organic solar cell, an organic diode, or an organic field effect transistor.

11. The square planar transition metal complex according to claim 5, wherein R1, R2, R3, and R4 are independently selected from pentafluorophenyl or tetrafluoropyridine.

12. The organic semiconductive material according to claim 7, wherein the molar doping ratio of dopant to matrix molecule or the doping ratio of dopant to monomeric units of a polymeric matrix molecule is between 10:1 and 1:1,000.

13. The organic semiconductive material according to claim 7 wherein the molar doping ratio of dopant to matrix molecule or the doping ratio of dopant to monomeric units of a polymeric matrix molecule is between 1:1 and 1:100.

* * * * *